(12) United States Patent
Eastwood

(10) Patent No.: US 8,993,958 B2
(45) Date of Patent: Mar. 31, 2015

(54) ANALYZING TARGET ANALYTES IN A SAMPLE USING MASS SPECTROSCOPY

(71) Applicant: Martin Eastwood, Stockport (GB)

(72) Inventor: Martin Eastwood, Stockport (GB)

(73) Assignee: Micromass UK Limited (GB)

( * ) Notice: Subject to any disclaimer, the term of this patent is extended or adjusted under 35 U.S.C. 154(b) by 0 days.

(21) Appl. No.: 13/895,738

(22) Filed: May 16, 2013

(65) Prior Publication Data

US 2013/0306853 A1    Nov. 21, 2013

Related U.S. Application Data

(60) Provisional application No. 61/648,413, filed on May 17, 2012.

(51) Int. Cl.
*H01J 49/00* (2006.01)
*H01J 49/04* (2006.01)
*G01N 33/68* (2006.01)
*G01N 33/74* (2006.01)

(52) U.S. Cl.
CPC .............. *H01J 49/0036* (2013.01); *H01J 49/04* (2013.01); *G01N 33/6851* (2013.01); *G01N 33/743* (2013.01)
USPC ............................ 250/282; 250/281; 250/288

(58) Field of Classification Search
CPC .............. G01N 33/743; G01N 33/6848; H01J 49/0036; H01J 49/00; H01J 49/26; H01J 49/0031; H01J 49/004
USPC .................................................. 250/281–300
See application file for complete search history.

(56) References Cited

U.S. PATENT DOCUMENTS

2008/0272293 A1* 11/2008 Vestal ............................ 250/288
2010/0047849 A1*  2/2010 Caulfield et al. ................ 435/29
2011/0240842 A1* 10/2011 Grant et al. ................... 250/282

OTHER PUBLICATIONS

Lin et al. "Measurement of urinary free cortisol by UPLC-tandem mass spectrometry", Clinical Chemistry, vol. 57, No. 10, Supplement, 2011. p. A191.*
Taylor et al. "Validation of a high-Throughput Liquid Chromatography-Tandem Mass Spectroscopy Method for Urinary Cortisol and Cortisone", Endocrinology and Metabolism, Clinical Chemistry 48:9 1511 (2002).*

(Continued)

*Primary Examiner* — Michael Logie
(74) *Attorney, Agent, or Firm* — McCarter & English, LLP

(57) ABSTRACT

A method for determining an amount of an analyte in a sample by mass spectrometry can include the steps of (i) ionizing an analyte from the sample and a deuterated analog of the analyte, to produce an analyte ion and a deuterated analog ion, where the deuterated analog undergoes fragmentation and deuterium scattering during mass spectrometry; (ii) measuring an analyte ion signal and a deuterated analog ion signal by mass spectrometry, where the deuterated analog ion signal is measured using a mass transition resulting from fragmentation and deuterium scattering; and (iii) determining an amount of analyte in the sample using the analyte ion signal and the deuterated analog ion signal. Corresponding kits can include instructions for carrying out the method, together with a deuterated analog of the analyte selected to undergo fragmentation and deuterium scattering during mass spectrometry and exhibit a mass transition resulting from fragmentation and deuterium scattering.

21 Claims, 4 Drawing Sheets

(56) References Cited

OTHER PUBLICATIONS

Duxbury et al., "Naturally occuring isotopes of an analyte can interfere with doubly deuterated internal standard measurements" Ann. Clin. Biochem. 2008.*

Percy et al., "MRM methods for high precision shift measurements in H/DX-MS", International Journal of Mass spectrometry 302 (2011) 26-35.*

Percy et al. "Surrogate H/D Detection Strategy for Protein Conformation Analysis Using MS/MS Data", Anal. CHem. 2009, 81, 7900-7900.*

"Mitagation of Deuterium Scrambling in Stable-Labeled Internal Standards during LC-MS/MS Analysis", XP055083265; Jan. 1, 2011.

Ikegawa et al., "Synthesis of 3- and 21-monosulfates of [2,2,3,4,4-H]-tetrahydrocorticosteroids in the 5-series as internal standards for mass spectrometry", Steroids, Elsevier Science Publishers, New York, NY, US, vol. 76, No. 12, pp. 1232-1240 (2011).

Furguson et al., "Hydrogen/Deuterium Scrambling during Quadruple Tome-of-Flight MS/MS Analysis of a Zinc-Binding Protein Domain", Analytical Chemistry, vol. 79, No. 1, pp. 153-160 (2007).

* cited by examiner

Compound name: Cortisol (1)
Correlation coefficient: r = 0.999848, r^2 = 0.999697
Calibration curve: 0.318595* x + -0.0493016
Response type: Internal Std (Ref 2), Area * (IS Conc. / IS Area)
Curve type: Linear, Origin: Exclude, Weighting: 1/x, Axis trans: None

US 8,993,958 B2

ANALYZING TARGET ANALYTES IN A SAMPLE USING MASS SPECTROSCOPY

RELATED APPLICATION

This application claims the benefit of U.S. Provisional Patent Application Ser. No. 61/648,413, filed May 17, 2012, which is incorporated herein by reference in its entirety.

FIELD OF THE INVENTION

The invention relates generally to analyzing an analyte in a sample using mass spectroscopy. The invention relates more particularly to mass spectrometry analysis where ionizing an analyte from the sample and a deuterated analog of the analyte produces a deuterated analog ion, where the deuterated analog undergoes fragmentation and deuterium scattering during mass spectrometry, and where the deuterated analog ion is monitored using a mass transition resulting from fragmentation and deuterium scattering.

BACKGROUND OF THE INVENTION

Mass spectrometry (MS) is a major discovery tool in the life sciences. MS analyzes the molecular composition of a sample by ionizing the sample or the analyte molecules contained in the sample and then measuring the mass-to-charge ratios of the resulting ions. The mass spectra obtained by MS can be used to identify, characterize, and/or quantify the analytes of interest. In particular, variants of liquid chromatography-mass spectrometry (LC-MS) have been used for quantification of biomarkers and biologically active compounds, due to the high selectivity, sensitivity, speed, and simplicity of LC-MS.

However, MS has weaknesses and limitations. For example, matrix effects and isobaric interferences can present challenges to MS analysis, especially in complex samples.

Complex samples can include complex matrices that can interfere with a target analyte signal. Matrix effects can alter the signal response (e.g., by affecting the ionization efficiency of target analytes during MS), potentially leading to erroneous results and thus resulting in poor analytical accuracy, linearity, and reproducibility. Matrix effects can also obscure the signal at a particular mass transition of interest, rendering MS incapable of studying certain analytes in certain samples.

Internal standards are often added to samples in an attempt to address matrix effects. For example, internal standards can include isotopically (e.g., deuterium) labeled analogs of the target analyte, which can be used to correct for signal deviation because they are present in known amounts and possess similar chemical properties to the non-labeled analyte. However, deuterated internal standards, despite their common use, can be subject to deuterium scattering, which is generally considered to increase unpredictability and raise questions about the validity of experimental data.

In addition to matrix effects and the challenges posed by deuterium scattering, isobaric interferences can interfere with MS analysis. Such interferences can result, for example, from the presence of ions of identical mass to the analyte of interest. Because samples (e.g., biological or clinical samples) often contain a complex array of matrix components, isobaric interferences can complicate or hinder measurement of the internal standard, thereby preventing the signal deviation caused by matrix effects from being rectified.

SUMMARY OF THE INVENTION

The invention provides for methods, materials, kits, and apparatuses for analyzing an analyte in a sample using mass spectroscopy. The invention advantageously harnesses (the generally undesired phenomenon of) deuterium scattering to address signal issues such as matrix effects and/or isobaric interference from the sample.

For example, a deuterated analog of the analyte (e.g., present in the sample as an internal standard) can exhibit deuterium scattering, resulting in a mass transition that would not have been expected based upon the structure of deuterated analog alone (e.g., deuterium scattering changes the position of at least one deuterium atom, thereby changing the mass of the deuterated analog ion by at least one mass unit). This "unexpected" mass transition can be used to measure the deuterated analog, in particular where the expected mass transition (e.g., indicative of no deuterium scattering) is obscured, for example by matrix effects and/or isobaric interference from the sample.

In other words, the invention provides for mass spectroscopy analysis where ionizing an analyte from the sample and a deuterated analog of the analyte produces a deuterated analog ion, where the deuterated analog undergoes fragmentation and deuterium scattering during mass spectrometry, and where the deuterated analog ion is monitored using a mass transition resulting from fragmentation and deuterium scattering.

Therefore, where conventional methods generally endeavor to avoid/minimize complex sample matrices and analyte deuterium scattering, the present invention can use these phenomena to its benefit. Accordingly, advantages of the invention include improved MS methods that can overcome issues associated with matrix effects, deuterium scattering, and isobaric interference.

In one aspect, the invention includes a method for determining an amount of an analyte in a sample by mass spectrometry. The method includes ionizing an analyte from the sample and a deuterated analog of the analyte, to produce an analyte ion and a deuterated analog ion, where the deuterated analog undergoes fragmentation and deuterium scattering during mass spectrometry. The method also includes measuring an analyte ion signal and a deuterated analog ion signal by mass spectrometry, where the deuterated analog ion signal is measured using a mass transition resulting from fragmentation and deuterium scattering. Furthermore, the method includes determining an amount of analyte in the sample using the analyte ion signal and the deuterated analog ion signal.

In another aspect, the invention includes a method for determining an amount of cortisol in a sample by mass spectrometry. The method includes ionizing cortisol from the sample and a deuterated cortisol analog, to produce a cortisol ion and a deuterated cortisol analog ion, where the deuterated cortisol analog undergoes fragmentation and deuterium scattering during mass spectrometry. The method also includes measuring a cortisol ion signal and a deuterated cortisol analog ion signal by mass spectrometry, where the deuterated cortisol analog ion signal is measured using a mass transition resulting from fragmentation and deuterium scattering. Furthermore, the method includes determining an amount of cortisol in the sample using the cortisol ion signal and the deuterated cortisol ion signal.

In still another aspect, the invention includes a kit for determining an amount of an analyte in a sample by mass spectrometry. The kit includes a deuterated analog of the analyte and instructions for using the deuterated analog to determine an amount of an analyte in a sample by mass spectrometry. The deuterated analog of the analyte can be selected to undergo fragmentation and deuterium scattering during mass spectrometry and exhibit a mass transition resulting from fragmentation and deuterium scattering. The instructions can include protocols for (i) ionizing an analyte from the sample and a deuterated analog of the analyte, to produce a analyte ion and a deuterated analog ion, (ii) measuring an analyte ion signal and a deuterated analog ion signal by mass spectrometry, where the deuterated analog ion signal is measured using the mass transition resulting from fragmentation and deuterium scattering, and (iii) determining an amount of analyte in the sample using the analyte ion signal and the deuterated analog ion signal.

In various embodiments, the mass spectrometry of one or more of the above aspects of the invention features collision induced dissociation (CID) mass spectrometry.

In some embodiments, the deuterated analog ion of one or more of the above aspects of the invention features a fragment ion. The fragmentation and deuterium scattering can result in the rearrangement of at least one deuterium atom from the fragment ion to a water molecule. The fragmentation and deuterium scattering can result in the rearrangement of at least one deuterium atom from the fragment ion to a second fragment ion. The fragmentation and deuterium scattering can result in the rearrangement of at least one deuterium atom from a second fragment ion to the fragment ion.

In certain embodiments, the deuterated analog of one or more of the above aspects of the invention features a non-hydrogen stable isotope label.

In various embodiments, the deuterated cortisol analog of one or more of the above aspects of the invention features d4-cortisol. In such embodiments, the mass transition can include an m/z of about 367>312. The mass transition can be about 367.1>312.1.

In some embodiment, the deuterated cortisol analog of one or more of the above aspects of the invention features d2-cortisol. In such embodiments, the mass transition can include an m/z of about 365>312. The mass transition can be about 365.1>312.1.

In certain embodiments, the term about, as used in connection with describing an m/z value can mean that the experimental value is the same, or essentially the same, as the recited value within the resolution of the MS device (e.g., to the theoretical resolution of the device, the practical resolution of the device, the resolution of the device as calibrated, and/or the resolution of the device for a given sample). Alternatively, the term about, as used in connection with describing an m/z value can mean that the experimental value is numerically the same as the recited value to the 1, 0.1, 0.001, or 0.0001 place.

In various aspects and embodiments, the invention advantageously overcomes matrix effects and/or isobaric interferences in complex samples that can present challenges to convention MS analysis. For example, the invention can overcome matrix effects that interfere with a target analyte signal. In various aspects and embodiments, the invention can overcome undesired deuterium scattering and/or isobaric interferences that can interfere with MS analysis.

The present invention is described in further detail by the figures and examples below, which are used only for illustration purposes and are not limiting.

Other features and advantages of the instant invention will be apparent from the following detailed description and claims.

DETAILED DESCRIPTION OF THE INVENTION

The invention provides for methods, materials, kits, and apparatuses for analyzing an analyte in a sample using mass spectroscopy together with a deuterated analog of the analyte that can exhibit deuterium scattering.

In various embodiments, the invention provides for MS analysis where ionizing an analyte from the sample and a deuterated analog of the analyte (e.g., internal standard) produces a deuterated analog ion, where the deuterated analog undergoes fragmentation and deuterium scattering during mass spectrometry, and where the deuterated analog ion is monitored using a mass transition resulting from fragmentation and deuterium scattering. Methods of the invention can also include one or more sample preparation, extraction, chromatography, and data analysis steps in connection with the MS analysis. Furthermore, the invention provides methods for identifying and/or selecting suitable deuterated analog ions. In its various embodiments, the invention can improve MS analysis, for example, by addressing matrix effects and/or isobaric interference.

Figure 1:
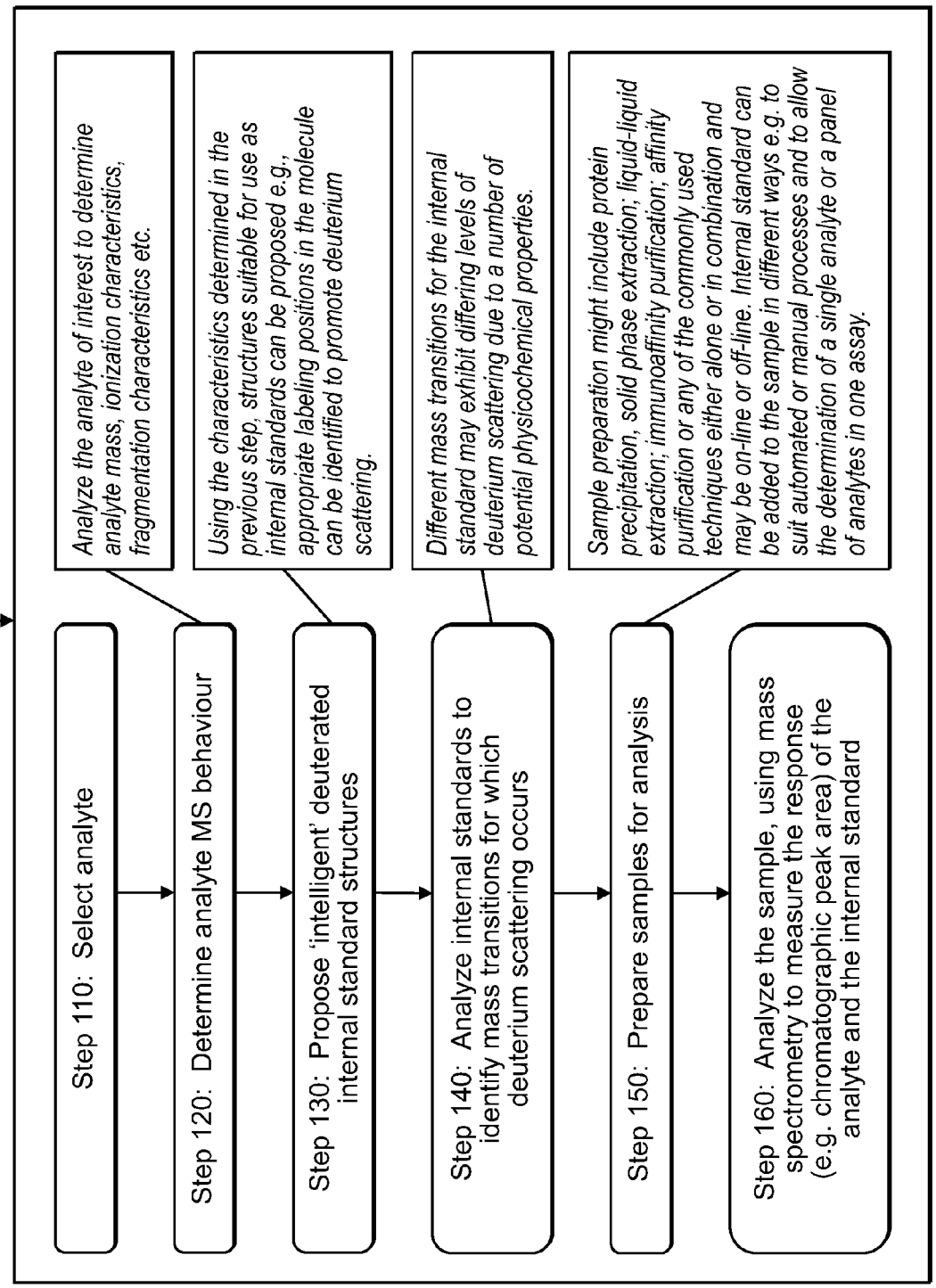
FIG. 1 illustrates an example methodology integrating various features of the invention.

FIG. 1 illustrates an example methodology 100 integrating various features of the invention, including analyte selection, internal standard selection, sample processing, and sample analysis. While the example methodology 100 is presented linearly, numerous additional embodiments are possible, including embodiments using a subset of the steps of methodology 100, different steps, additional steps, repeating steps, and combinations thereof.

Step 110 includes selecting an analyte. Analytes or target analytes can include essentially any molecule of interest that can be detected in a mass spectrometer. The target analyte can be of interest in one or more of clinical chemistry, medicine, veterinary medicine, forensic chemistry, pharmacology, food industry, safety at work, and environmental pollution. In general, the target analyte is an organic molecule. Further examples of suitable analytes and samples are described in the Analytes and Samples sections below.

Step 120 includes determining an analyte's MS behavior. For example, step 120 can include analyzing the analyte to determine the analyte's mass, ionization characteristics, fragmentation characteristics, and the like. Step 120 can include analyzing the behavior of the analyte in the sample, e.g., to identify matrix effects and/or isobaric interference. Example MS analysis are described in the Mass Spectroscopy and Examples sections below.

Step 130 includes proposing at least one deuterated internal standard structure. For example, a user can employ the information from step 120 to arrive at an informed hypothesis as to which position(s) of the target analyte molecule should be deuterated to produce the internal standard. The position(s) can be selected based upon the knowledge, or expectation, that deuterium at the position(s) will undergo deuterium scattering. In this regard, step 130 stands in contrast to many prior art methods, which endeavor to minimize or, if possible, avoid deuterium scattering.

Step 140 includes analyzing the internal standard(s) proposed in step 130, to identify the one or more mass transitions indicative of deuterium scattering. The different mass transitions for each proposed internal standard can exhibit differing levels of deuterium scattering due to a number of potential physicochemical properties, such as proximity to polar groups.

Examples of proposing and analyzing deuterated analogs are discussed in further detail in the Deuterated Analogs and Internal Standards, Deuterium Scattering and Development of Deuterated Analogs, and Examples sections below.

If step 140 identifies a usable, deuterated internal standard for a target analyte, then a sample suspected of including the target analyte can be analyzed using the deuterated internal standard. However, if the proposed internal standard is deemed unusable (e.g., based on the analysis of step 140), then steps 110-140 can be repeated to identify a usable internal standard.

Step 150 includes preparing a sample for analysis. In various embodiments, sample preparation can be tailored to the properties of the sample and/or the desired analysis, to include one or more of protein precipitation, solid phase extraction, liquid-liquid extraction, immunoaffinity purification, affinity purification, or any other sample preparation techniques known in the art. Sample preparation can be carried out on-line or off-line. An internal standard can be added to the sample during sample preparation, for example in an automated or manual processes and/or to allow the analysis of a single analyte or a panel of analytes in a single assay. Further examples of sample preparation are described in the Sample Preparation and Separation section below.

Step 160 includes analyzing a sample using mass spectrometry to measure the response (e.g. chromatographic peak area) of an analyte and a duterated internal standard for the analyte. For example, a deuterated analog of the analyte (e.g., present in the sample as an internal standard) can exhibit deuterium scattering, resulting in a mass transition that would not have been expected based upon the structure of deuterated analog alone (e.g., deuterium scattering changes the position of at least one deuterium atom, thereby changing the mass of the deuterated analog ion by at least one mass unit). This "unexpected" mass transition can be used to measure the deuterated analog, in particular where the expected mass transition (e.g., indicative of no deuterium scattering) is obscured, for example by matrix effects and/or interference from the sample. Example MS analysis are described in the Mass Spectroscopy and Examples sections below.

Analytes

Further to the summary above, analytes or target analytes can include essentially any molecule of interest that can be detected in a mass spectrometer. The target analyte can be of interest in one or more of clinical chemistry, medicine, veterinary medicine, forensic chemistry, pharmacology, food industry, safety at work, and environmental pollution. In general, the target analyte is an organic molecule which includes at least 1 carbon atom, such as 1, 2, 3, 4, 5, 6, 7, 8, 9, 10 or more carbon atoms. The target analyte can include up to 1,000, 100, 90, 80, 70, 60, 50, 45, 40, 35, 30, 25, 20, or 15 carbon atoms.

Clinical chemistry target analytes can include any organic compound present in an organism (e.g., human body, animal body, fungi, bacterium, virus, and the like). For example, clinical chemistry target analytes include, but are not limited to, nucleoside-bases (e.g., adenine, cytidine, guanine, thymine, uracil), their analogs (e.g., 7-deazaguanine), and derivatives (e.g., mono-, di-, triphosphates or cyclic phosphates); hormones (e.g., steroidal hormones); amino acids; proteins (e.g., brain natriuretic peptide); metabolites (e.g., creatinine, bilirubin); cardiac markers (e.g., creatinkinase-MB); liver markers (e.g., aspartate transaminase); neurotransmitter (e.g., GABA, glycine, biogenic amines (such as dopamine, norepinephrine, epinephrine, histamine, serotonin), acetylcholine, adenosine, anandamide); drugs and their metabolites (e.g., sedatives, tranquilizers, antihypertensives, narcotics).

Human medicine and veterinary medicine target analytes can include any organic compound that can be used for the diagnosis, prophylaxis or treatment of a disease or condition in a subject. For example, human medicine and veterinary medicine target analytes include, but are not limited to, disease markers (e.g., tumor-associated antigens); ultraviolet screening agents, contrast agents; prophylactic or therapeutic agents (e.g., allergens, antibiotics, antifungal agents, antibacterial agents, antihistaminic agents, antineoplastic agents, analgesics, anorexics, anthelmintics, anticonvulsants, antidepressants, antidiabetic agents, antidiarrheals, antihistamines, anti-inflammatory agents, antimigraine preparations, antinauseants, antiparkinsonism drugs, antipruritics, antipsychotics, antipyretics, antispasmodics, anticholinergics, sympathomimetics, xanthine derivatives, cardiovascular effective agents including calcium channel blockers, betablockers, antiarrhythmics, antihypertensives, diuretics, vasodilators; CNS stimulants, agents against cough and cold, decongestants, hormones, hypnotics, immunosuppressives, insect repellents, muscle relaxants, parasympatholytics, parasympathomimetics, psychostimulants, sedatives, tranquilizers, physiologically active peptides and proteins).

Forensic chemistry target analytes can include any organic compound present in a sample taken from the site of crime, such as a sample from a victim's body (e.g., tissue or fluid sample, hair, blood, semen, urine, and the like). For example, clinical chemistry target analytes include, but are not limited to, toxic agents, drugs and their metabolites (e.g., sedatives, tranquilizers, antihypertensives, and narcotics), nucleic acids, DNA, RNA, pesticides, natural products, pollutants, and industrial compounds.

Pharmacology target analytes can include any organic compound that is a pharmaceutical or metabolite thereof or which can be used for the design, synthesis, and monitoring of drugs. For example, pharmacology target analytes include, but are not limited to, prophylactic and/or therapeutic agents, their prodrugs, intermediates and metabolites.

Food industry and agricultural target analytes can include any organic compound that is relevant for monitoring of the safety of foods, beverages, and/or other food industry/agricultural products. Examples of target analytes from the field of food industry include, but are not limited to, steroids, plasticizers, pathogen markers, pesticides, fungicides, pollutants, allergens (e.g. gluten and nut proteins), mycotoxins and marine toxins, as well as antibiotics (e.g., chloramphenicol in shrimp).

Workplace safety target analytes can include any organic potentially hazardous compound which may be present at a workplace. For example, workplace safety target analytes include, but are not limited to, solvents, low volatile substances, pollutants, carcinogens, toxins, pesticides, fungicides, and any organic substance for which an occupational exposure limit has been set (e.g., by a business, governmental, regulatory, or administrative body).

Environmental pollution (or industrial) target analytes can include any organic compound which can be hazardous for the environment (e.g., organisms in the environment). For example, environmental pollution (or industrial) target analytes include, but are not limited to, persistent organic pollutants (such as aldrin, chlordane, DDT, dieldrin, endrin, heptachlor, hexachlorobenzene, mirex, polychlorinated biphenyls, polychlorinated dibenzo-p-dioxins, polychlorinated dibenzofurans, and toxaphene), polycyclic aromatic hydrocarbons (such as benz[a]anthracene and chrysene), volatile organic compounds, and environmental xenobiotics (such as analgesics, e.g., acetaminophen, acetylsalicylic acid, diclofenac, codeine, ibuprofen; antibiotics, e.g., macrolide antibiotics, sulfonamides, fluoroquinolones, chloramphenicol, tylosin, trimethoprim, erythromycin, lincomycin, sulfamethoxazole, trimethoprim; anticonvulsant, e.g., carbamazepine, primidone; beta-blockers, e.g., metoprolol, propanolol, betaxolol, bisoprolol, nadolol; X-ray media, e.g., iopromide, iopamidol, iohexyl, diatrizoate; cytostatics; steroids and hormones, e.g., 17α-ethinylestradiol, mestranol, 19-norethisterone). Analytes can also include inorganic analytes (e.g., phosphorous compounds, silicon compounds, inorganic polymers, and the like). Analytes can also include oils and petrochemicals (e.g., mineral oils and the like).

Target analytes can include amino acids (e.g., Gly, Ala, Val, Leu, Ile, Pro, Phe, Trp, Cys, Met, Ser, Thr, Tyr, His, Lys, Arg, Asp, Glu, Asn, Gln, selenocysteine, ornithine, citrulline, hydroxyproline, hydroxyproline, methyllysine, carboxyglutamate), peptides, polypeptides, proteins, glycoproteins, lipoproteins; nucleotides, oligonucleotides, polynucleotides, nucleic acids, DNA, RNA, peptide-nucleic acids; sugars, mono-, di-, oligo-, polysaccharides, starches, complex carbohydrates; lipids, fatty acids, fats, complex lipids, steroids; vitamins (A, $B_1$, $B_2$, $B_6$, $B_9$, $B_{12}$, C, D, $D_2$, E, F, K, $K_1$, $K_2$); hormones (such as peptide hormones (e.g., TRH and vasopressin), lipid hormones (e.g., steroid hormones and eicosanoids), monoamines derived from aromatic amino acids (e.g., thyroxine and adrenaline)), androgens (e.g., anabolic steroids, androstenedione, dehydroepiandrosterone, dihydrotestosterone, testosterone), estrogens (e.g., estradiol, estriol, estrone, 17α-ethinylestradiol, mestranol), progestagens (e.g., progesterone, 19-norethisterone), progestins (e.g., norethindrone, norethynodrel, norethindrone acetate, ethynodiol diacetate, levonorgestrel, norethisterone, norgestrel, desogestrel, gestodene, norgestimate, drospirenone, dienogest, drospirenone, nestorone, nomegestrol acetate and trimegestone); steroids, such as insect steroids (e.g., ecdysterone), vertebrate steroids (e.g., sex steroids/hormones, corticosteroids (including glucocorticoids and mineralocorticoids (e.g., hydrocortisone, cortisone, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, dexamethasone, fluocortolone, hydrocortisone-17-butyrate, hydrocortisone-17-valerate, aclometasone dipropionate, flunisolide, beclomethasone dipropionate)), anabolic steroids (e.g., testosterone, nortestosterone, and their derivatives (such as alkylation (e.g., methyl or ethyl) at 17-alpha position, or esterification at the 17-beta position)), cholesterol and derivatives thereof (e.g., oxysterols and bile acids)), plant steroids (such as phytosterols and brassinosteroids (e.g., β-sitosterol, campesterol, stigmasterol, brassicasterol)), fungus steroids (such as ergosterols); industrial polymers (such polyvinylchloride, polyethylene terephthalate, polyacrylamide) and their monomers; small organic molecules such as drugs and drug-like molecules or fragments thereof.

In various embodiments, target analytes of particular interest include steroids (preferably steroid hormones or sex hormones, such as testosterone, cortisol, estrone, estradiol, 17-OH-progesterone or aldosterone); immunosuppressant drugs (such as cyclosporin A, tacrolimus, sirolimus, everolimus, or mycophenolic acid); thyroid markers (such as thyroid-stimulating hormone (TSH), thyroglobulin, triiodothyronine (T3), free T3, thyroxine (T4), free T4, or ferritin); vitamins or metabolites thereof (such as the 25-hydroxy-, 1,25-dihydroxy- or 24,25-dihydroxy-form of vitamin D2 or vitamin D3); cardiac markers (such as troponins or brain natriuretic peptide); alpha-fetoprotein; applipoprotein, or drugs of abuse (such as hydromorphone, other opiod drugs, or therapeutic drugs).

Samples

In general, a sample is a composition including at least one target analyte (e.g., an analyte of the class or kind disclosed above, together with a matrix). Samples can include a solid, liquid, gas, mixture, material (e.g., of intermediary consistency, such as a, extract, cell, tissue, organisms) or a combination thereof. In various embodiments, the sample is a bodily sample, an environmental sample, a food sample, a synthetic sample, an extract (e.g., obtained by separation techniques), or a combination thereof.

Bodily samples can include any sample that is derived from the body of an individual. In this context, the individual can be an animal, for example a mammal, for example a human. Other example individuals include a mouse, rat, guinea-pig, rabbit, cat, dog, goat, sheep, pig, cow, or horse. The individual can be a patient, for example, an individual suffering from a disease or being suspected of suffering from a disease. A bodily sample can be a bodily fluid or tissue, for example taken for the purpose of a scientific or medical test, such as for studying or diagnosing a disease (e.g., by detecting and/or identifying a pathogen or the presence of a biomarker). Bodily samples can also include cells, for example, pathogens or cells of the individual bodily sample (e.g., tumor cells). Such bodily samples can be obtained by known methods including tissue biopsy (e.g., punch biopsy) and by taking blood, bronchial aspirate, sputum, urine, feces, or other body fluids. Exemplary bodily samples include humor, whole blood, plasma, serum, umbilical cord blood (in particular, blood obtained by percutaneous umbilical cord blood sampling PUBS), cerebrospinal fluid (CSF), saliva, amniotic fluid, breast milk, secretion, ichor, urine, faeces, meconium, skin, nail, hair, umbilicus, gastric contents, placenta, bone marrow, peripheral blood lymphocytes (PBL), and solid organ tissue extract.

Environmental samples can include any sample that is derived from the environment, such as the natural environment (e.g., seas, soils, air, and flora) or the manmade environment (e.g., canals, tunnels, buildings). Such environmental samples can be used to discover, monitor, study, control, mitigate, and avoid environmental pollution. Exemplary environmental samples include water (e.g., drinking water, river water, surface water, ground water, potable water, sewage, effluent, wastewater, or leachate), soil, air, sediment, biota (e.g., soil biota), flora, fauna (e.g., fish), and earth mass (e.g., excavated material).

Food samples can include any sample that is derived from food (including beverages). Such food samples can be used for various purposes including, for example, (1) to check whether a food is safe; (2) to check whether a food contained harmful contaminants at the time the food was eaten (retained samples) or whether a food does not contain harmful contaminants, (3) to check whether a food contains only permitted additives (e.g., regulatory compliance); (4) to check whether it contains the correct levels of mandatory ingredients (e.g., whether the declarations on the label of the food are correct), or (5) to analyze the amounts of nutrients contained in the food. Exemplary food samples include edible products of animal, vegetable or synthetic origin (e.g., milk, bread, eggs, or meat), meals, drinks, and parts thereof, such as retain samples. Food samples can also include fruits, vegetables, pulses, nuts, oil seeds, oil fruits, cereals, tea, coffee, herbal infusions, cocoa, hops, herbs, spices, sugar plants, meat, fat, kidney, liver, offal, milk, eggs, honey, fish, and beverages.

Synthetic samples can include any sample that is derived from an industrial process. The industrial process can be a biological industrial process (e.g., processes using biological material containing genetic information and capable of reproducing itself or being reproduced in a biological system, such as fermentation processes using transfected cells) or a non-biological industrial process (e.g., the chemical synthesis or degradation of a compound such as a pharmaceutical). Synthetic samples can be used to check and monitor the progress of the industrial process, to determine the yield of the desired product, and/or measure the amount of side products and/or starting materials.

Sample Preparation and Separation

In various embodiments, the methods can include one or more additional steps before mass spectrometry. Additional steps can be conducted manually or can be automated (e.g., in a specifically programmed or specifically built machine).

In one embodiment, the method includes preparing a sample by combining known quantities of a specimen potentially comprising a target analyte and a deuterated analog for the target analyte. Suitable sample preparation can vary depending upon the nature of the sample and analytical protocol. For example, sample preparation can include selecting one or more suitable analogs, selecting an analytical panel, and/or selecting the amounts of the various analogs.

In another embodiment, the method also includes processing the sample prior to obtaining the mass spectrometer signal. For example, processing the sample can include separating the target analyte from other components of sample. Processing can be performed by techniques commonly used for processing samples prior to MS analysis, or by a combination of such techniques, in order to (1) reduce the number of compounds introduced into the mass spectrometer; (2) concentrate the target analyte(s), e.g., by depleting unwanted compounds and/or enrichment of a target analyte; and/or (3) separate the analog from other compounds that could interfere with the MS analysis. Such techniques can include one or more of solid phase extraction, liquid phase extraction, and chromatography (e.g., liquid, gas, affinity, immuno affinity, and supercritical fluid chromatography).

Accordingly, separation systems can include one or more extraction, separation, chromatography, or similar systems (e.g., solid phase extraction, liquid chromatography, gas chromatography, affinity, immunoaffinity, supercritical fluid chromatography equipment, and the like) for separating the analog(s) and/or corresponding target analyte(s) from other components of the single sample prior to obtaining a mass spectrometer signal. Separation systems can separate one or more analog(s)/analyte(s) from each other and/or from at least a portion of the sample (e.g., matrix, contaminants). For example, at least a portion of a sample can be processed by solid-phase extraction (e.g., normal phase solid-phase extraction (SPE), reversed phase SPE, ion-exchange SPE, size exclusion SPE, affinity SPE or a combination thereof), liquid-liquid extraction, chromatography (e.g., liquid chromatography such as HPLC, for example, Waters® ACQUITY UPLC®, Supercritical Fluid Chromatography (SFC), carbon dioxide based chromatography (i.e., carbon dioxide used as at least a portion of the mobile phase), Ultra High Performance Liquid Chromatography (UHPLC), nano-LC, in particular normal phase chromatography, reversed phase chromatography, ion-exchange chromatography, size-exclusion chromatography, affinity chromatography) or gas chromatography), electrophoresis (e.g., capillary electrophoresis), precipitation, derivatization, or any combination thereof. The extraction, chromatography, or electrophoresis device may be coupled to a mass spectrometer (on-line mode) or not (off-line mode).

Mass Spectroscopy

Different methods for obtaining a mass spectrometer signal are known in the art. In various implementations, mass spectrometric analysis includes ionizing one or more compounds to generate charged molecules or molecule fragments and measuring their mass-to-charge ratios (cf. Sparkman, O. D. (2000). Mass spectrometry desk reference. Pittsburgh: Global View Pub. ISBN 0-9660813-2-3). Such procedures can include the following steps: loading a mixture containing one or more compounds onto the MS instrument and vaporizing the one or more compounds; ionizing the components of the mixture, to form charged particles (ions); electromagnetically separating the ions according to their mass-to-charge ratio in an analyzer; detecting the ions (e.g., by a quantitative method); and transforming the ion signals into mass spectra.

The mass spectrometer can be operated, for example, in any of the following modes: (1) full scan, e.g., the mass spectrometer detects all ions between two distant points on the m/z scale (such as 0 and 10000); (2) Single Ion Monitoring (SIM) or Single Ion Recording (SIR), e.g., the mass spectrometer detects only ions which have a particular m/z value or which lie within a small m/z range (e.g., a range of 1 or 2 mass units); (3) Multiple Reaction Monitoring (MRM), e.g., in a mass spectrometer having multiple mass spectrometer units, at least two units are operated in the SIM/SIR mode.

After separation and measurement of the intensities of the ions in the mass spectrometer, mass spectra are created, for example by plotting the intensities measured for the detected ions vs. their mass-to-charge ratio (m/z). Depending on the mode by which the mass spectrometer is operated (full scan, SIM/SIR, or MRM), the mass spectra can include (1) the peaks corresponding to all ions (precursor and product ions) detected in the mass spectrometer between two distant points on the m/z scale; (2) the peaks corresponding to (a) all ions which have a particular m/z value or which lie within a very small mass m/z range and optionally (b) all product ions derived from the ions specified under (a); or (3) only one or more selected product/daughter ions (MRM channels).

For example, when the mass spectrometer is operated in MRM mode, one can create a single mass spectrum for a deuterated analog and corresponding target analyte. The single mass spectrum will contain one peak for each analog and, if present in the sample, one peak for the corresponding target analyte. Alternatively, multiple mass spectra can be created for each analog and each corresponding target analyte, where each of the multiple mass spectra only represents one analog or target analyte. Such single mass spectrum or multiple mass spectra can be created for each analog and corresponding target analyte (e.g., in a panel).

Mass spectra created using MRM channels and where peak intensities are plotted against time (such as retention time if the mass spectrometer is coupled to a SPE, chromatography, or electrophoresis device) are often described as mass chromatograms. Thus, the term mass spectra, as used herein, can also relate to mass chromatograms (e.g., where the MS operates in MRM mode).

Next, the MS signal intensities (or relative signal intensities) of the ions representative of each of the target analyte(s) and corresponding analog(s) are determined. The signal intensities of the ions in the mass spectra (e.g., the intensities of the peaks corresponding to these ions) can be determined on the basis of the peak height or peak area, for example on the basis of peak area such as by integrating the signal intensity of a specific ion with respect to time. The intensities of the ions signals in the mass spectrum/spectra can be normalized e.g., to 100%, to the most intense ion signal detected.

The mass spectrometer (as well as the mass spectrometers of any of the methods of the invention) can be essentially any instrument that includes an ionization source, an analyzer, and a detector suitable for producing mass spectra. The mass spectrometer may contain multiple mass spectrometer units (MSn where n=2, 3, 4 . . . ) and/or can be coupled to other instruments, such as a chromatography or electrophoresis device (e.g., a separation system, for example in LC/MS/MS).

The mass spectrometer can include an ion source such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionization ("DESI") ion source; a Nickel-63 radioactive ion source; an Atmospheric Pressure Matrix Assisted Laser Desorption Ionization ion source; and a Thermospray ion source.

The mass spectrometer can include a mass analyzer such as a quadrupole mass analyzer; a 2D or linear quadrupole mass analyzer; a Paul or 3D quadrupole mass analyzer; a 2D or linear quadrupole ion trap mass analyzer; a Paul or 3D quadrupole ion trap mass analyzer; a Penning trap mass analyzer; an ion trap mass analyzer; a magnetic sector mass analyzer; Ion Cyclotron Resonance ("ICR") mass analyzer; a Fourier Transform Ion Cyclotron Resonance ("FTICR") mass analyzer; an electrostatic or orbitrap mass analyzer; a Fourier Transform electrostatic or orbitrap mass analyzer; a Fourier Transform mass analyzer; a Time of Flight mass analyzer; an orthogonal acceleration Time of Flight mass analyzer; and a linear acceleration Time of Flight mass analyzer. The mass spectrometer can include an ion mobility analyzer.

The mass spectrometer can include an ionization source such as an Electrospray ionization ("ESI") ion source; an Atmospheric Pressure Photo Ionization ("APPI") ion source; an Atmospheric Pressure Chemical Ionization ("APCI") ion source; a Matrix Assisted Laser Desorption Ionization ("MALDI") ion source; a Laser Desorption Ionization ("LDI") ion source; an Atmospheric Pressure Ionization ("API") ion source; a Desorption Ionization on Silicon ("DIOS") ion source; an Electron Impact ("EI") ion source; a Chemical Ionization ("CI") ion source; a Field Ionization ("FI") ion source; a Field Desorption ("FD") ion source; an Inductively Coupled Plasma ("ICP") ion source; a Fast Atom Bombardment ("FAB") ion source; a Liquid Secondary Ion Mass Spectrometry ("LSIMS") ion source; a Desorption Electrospray Ionization ("DESI") ion source; a Nickel-63 radioactive ion source; an Atmospheric Pressure Matrix Assisted Laser Desorption Ionization ion source; and a Thermospray ion source.

Deuterated Analogs and Internal Standards

Deuterated analogs (e.g., internal standards) are compounds which are similar to a corresponding target analyte with respect to chemical composition (e.g., empirical formula), structure (e.g., atomic arrangement and bonding), and/or physicochemical properties, but which include at least one position that is deuterated in the analog but not in the target analyte. The deuterated analog and corresponding target analyte are distinguishable by their behavior in a mass spectrometer.

In various embodiments, the only chemical difference between the analog and analyte is the deuteration of at least one position in the analog. However, in some embodiments, further differences are possible. For example, the analog and analyte can have at least the same base structure in common (e.g., a characteristic mono- or polycyclic ring structure, such as sterane). In many embodiments, the compounds can differ slightly with respect to their chemical composition and/or molecular mass (i.e., in addition to deuteration). For example, difference in composition and/or mass can result from (i) replacement of one group with a homologous group (e.g., a homologous group can have 1 carbon atom more or less (e.g., ethyl (ethylene) can be considered a homologue to methyl and propyl (methylene and propylene)); (ii) modification of a functional group (e.g., acetylation of an amino group; esterification; methylation; hydroxylation; hydration; biotinylation; cleavage of an amide, ester, thioester, acetal, ketal group; decarboxylation; demethylation; dehydration); (iii) replacement of an atom with another atom of the same group of the period table of elements (e.g., replacement of one halogen with another); and (iv) replacement of an atom with a corresponding isotope of the atom (e.g., $^{12}C$ is replaced with $^{13}C$).

Furthermore, an analog can mimic a corresponding target analyte such that at least one of the physicochemical properties of the analog is essentially identical to the corresponding physicochemical property of the target analyte. Physicochemical properties can include any measurable property the value of which describes a physical and/or chemical state of a compound. For example, physicochemical properties include, but are not limited to, size, mass, absorbance, emission, electric charge, electric potential, isoelectric point (pI), flow rate (e.g., retention time), magnetic field, spin, solubility, viscosity, reactivity against or affinity to other substances (e.g., antibodies, enzymes), toxicity, chemical stability in a given environment, capability to undergo a certain set of transformations (e.g., molecular dissociation, chemical combination, redox reactions) under certain physical conditions in the presence of another chemical substance, polarity, and hydrophobicity/hydrophilicity.

In various embodiments, the analog and its corresponding target analyte are effectively indistinguishable from each other by one or more techniques commonly used to process a sample prior to mass spectrometric analysis. For example, an analog and its corresponding target analyte can be indistinguishable on the basis of solubility (in a solvent, e.g., water or an organic solvent, or a mixture of solvents), retention time (in a separation technique, such as liquid chromatography), affinity (e.g., to an antibody specific for the target analyte), dissociation constant, reactivity and/or specificity towards an enzyme (e.g., hydrolase, transferase).

The analog is generally absent or in a negligible (or otherwise compensable) initial amount in the sample to be analyzed. The analog can be a synthetic compound, e.g., a compound which does not naturally occur (e.g., in the sample) or the natural abundance of which is below the detection limit of a mass spectrometer. For example, an analog can be a deuterated and further isotope-labeled analog of the corresponding target analyte, a derivative of the corresponding target analyte, or a metabolite of the corresponding target analyte.

Isotopes include nuclides with the same number of protons but differing numbers of neutrons (i.e., they have the same atomic number and are therefore the same chemical element). Different isotopes of the same chemical element generally have essentially the same chemical characteristics and therefore behave essentially identically in chemical and/or biological systems. Therefore, isotope labeled analogs of a corresponding target analytes include compounds that are essentially identical to the target analyte in chemical composition and structure, with the exception that at least one atom of the target analyte is substituted for an isotope thereof.

In various embodiments, the at least one atom of the target analyte is the most abundant naturally occurring isotope and the substituted isotope of the analog is a less abundant isotope. For example, the target analyte can include a position with $^1H$ ($^{12}C$, $^{14}N$, $^{16}O$, or $^{80}Se$) and the analog can substitute the atom in that position for $^2H$ ($^{13}C$, $^{15}N$, $^{17}O$, $^{18}O$, $^{33}S$, $^{36}S$, and $^{74}Se$, respectively). The natural abundance of the isotope can be less than 49% (e.g., less than 40%, 30%, 20%, 10%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01% of the total amount of all existing isotopes). The isotope labeled analog can use a stable isotope.

A stable isotope of an atom can be non-radioactive or radioactive. If the stable isotope is radioactive, its half-life is too long to be measured, such as a half-life longer than the age of the universe, e.g., a half-life of $13.75 \times 10^9$ years or greater. Stable isotopes include, but are not limited to, $^2H$, $^6Li$, $^{11}B$, $^{13}C$, $^{15}N$, $^{17}O$, $^{18}O$, $^{25}Mg$, $^{26}Mg$, $^{29}Si$, $^{30}Si$, $^{33}S$, $^{34}S$, $^{36}S$, $^{37}Cl$, $^{41}K$, $^{42}Ca$, $^{43}Ca$, $^{44}Ca$, $^{46}Ca$, $^{48}Ca$, $^{46}Ti$, $^{47}Ti$, $^{49}Ti$, $^{50}Ti$, $^{50}V$, $^{50}Cr$, $^{53}Cr$, $^{54}Cr$, $^{54}Fe$, $^{57}Fe$, $^{58}Fe$, $^{60}Ni$, $^{61}Ni$, $^{62}Ni$, $^{64}Ni$, $^{65}Cu$, $^{66}Zn$, $^{67}Zn$, $^{68}Zn$, $^{70}Zn$, $^{71}Ga$, $^{73}Ge$, $^{76}Ge$, $^{74}Se$, $^{76}Se$, $^{77}Se$, $^{78}Se$, $^{82}Se$, $^{81}Br$, $^{84}Sr$, $^{96}Zr$, $^{94}Mo$, $^{97}Mo$, $^{100}Mo$, $^{98}Ru$, $^{102}Pd$, $^{106}Cd$, $^{108}Cd$, $^{113}In$, $^{112}Sn$, $^{112}Sn$, $^{114}Sn$, $^{115}Sn$, $^{120}Te$, $^{123}Te$, $^{130}Ba$, $^{132}Ba$, $^{138}La$, $^{136}Ce$, $^{138}Sn$, $^{148}Nd$, $^{150}Nd$, $^{144}Sm$, $^{152}Gd$, $^{154}Gd$, $^{156}Dy$, $^{158}Dy$, $^{162}Er$, $^{164}Er$, $^{168}Yb$, $^{170}Yb$, $^{176}Lu$, $^{174}Hf$, $^{180m1}Ta$, $^{180}W$, $^{184}OS$, $^{187}OS$, $^{190}Pt$, $^{192}Pt$, $^{196}Hg$, and $^{204}Pb$. Examples of preferred stable isotopes include $^2H$, $^{11}B$, $^{13}C$, $^{15}N$, $^{17}O$, $^{18}O$, $^{33}S$, $^{34}S$, $^{36}S$, $^{74}Se$, $^{76}Se$, $^{77}Se$, $^{78}Se$, and $^{82}Se$.

A given analog can be isotopically pure with respect to the atom in the substituted position(s). Isotopically pure can mean that at least 95% of atoms of a given type (e.g., a high abundant isotope such as $^1H$) contained in a compound (such as a target analyte) have been replaced with another, preferably less abundant, isotope of the same element (e.g., $^2H$). For example, at least 96%, 97%, 98%, 99%, 99.1%, 99.2%, 99.3%, 99.4%, 99.5%, 99.6%, 99.7%, 99.8%, 99.9%, 99.91%, 99.92%, 99.93%, 99.94%, 99.95%, 99.96%, 99.97%, 99.98%, or 99.99% or more of atoms of a given type can be replaced with another, preferably less abundant, isotope of the same element.

Derivatives of target analytes include compounds that are similar to the target analyte in chemical composition, except that they are derivatized. Derivatizing or derivatization relates to the transformation of a chemical compound (starting material) into a product, i.e., a derivative, having a similar structure to the starting material. A derivative can exhibit one or more altered (e.g., relative to the starting material) physicochemical properties, such as altered reactivity, solubility, boiling point, melting point, aggregate state, or chemical composition. Altered physicochemical properties can be used for quantification and/or separation of the derivative and/or starting material. Example of derivatization include reduction (with or without an enzyme), oxidation (with or without an enzyme), acylation (e.g., acetylation), alkylation (e.g., methylation), hydrolysis (e.g., of ester, amide, epoxide groups), addition (e.g., hydrogenation of double or triple bonds), condensation (e.g., generating an imine bond), elimination (e.g., reductive elimination or elimination of water), and substitution (e.g., nucleophilic or electrophilic substitution).

Metabolites include intermediates and products of metabolism, for example the transformation, degredation, and elimination of organic compound by natural (or engineered) biochemical process. Metabolites can be small molecules, e.g., having a molecular mass of below 1500 Da. Metabolites can be, or originate from, endogenous or exogenous (e.g., pharmaceutical) compounds.

The property of being distinguishable based upon behavior in a mass spectrometer includes situations where two or more compounds (such as an analog and corresponding target analyte) can be distinguished from each other by a mass spectrometer due to differences in their mass (i.e., a difference in mass that can be resolved by a MS instrument, or at a given cutoff) and/or fragmentation pattern.

For example, two compounds (e.g., the first internal calibrator and the target analyte) can be distinguished from each other by a mass spectrometer due to differences in their mass. The masses of the two compounds (e.g., the first internal calibrator and the target analyte) can differ in at least 1 (or 2, 3, 4, 5 . . . ) mass units where the compounds are isotopic analogs. A difference in mass can be less than one mass unit, or a non-integer mass unit greater than one. Depending upon instrument resolution and/or a desired resolution cutoff, a difference in mass can be a difference of ±0.1, 0.01, 0.001, 0.0001, 0.0001 mass units. The difference in mass between these two compounds can originate from the presence of different isotopes (e.g., low abundant isotopes in one of the two compounds vs. high abundant isotopes in the other of the two compounds) and/or different chemical moieties.

Any two compounds can also be distinguished from each other by a mass spectrometer due to differences in their fragmentation pattern. The fragmentation pattern of a compound relates to the compound-specific set of fragments (e.g., product/daughter ions) generated in a mass spectrometer from the compound. The two or more compounds (e.g., an analog and corresponding target analyte) can fragment during the MS analysis essentially in the same way, thereby generating fragments similar in chemical composition and structure. However, the fragment generated from one compound (e.g., the analog) can differ from the corresponding structurally similar fragment generated by the other compound (e.g., the corresponding target analyte) by a mass amount that can be resolved by the instrument being used and/or that meets a predetermined cutoff.

Deuterium Scattering and Development of Deuterated Analogs

Deuterium scattering is a phenomenon in which deuterium and hydrogen atoms appear to migrate across a molecule, for example, during collision-induced dissociation (CID) mass spectrometry. There have been a number of studies carried out to elucidate the mechanism of scattering but no consensus has been reached. See, for example, Jørgensen et al. JACS 127, 2785-2793 (2005); Demmers et al. JACS 124, 11191-11198 (2002); Bache et al. J. Am. Soc. Mass. Spec. 19, 1719-1725 (2008); and Abzalimov et al. Anal. Chem. 82, 942-950 (2010).

Much of the work investigating deuterium scattering has originated from mass spectrometry-based proteomics where scattering has become a notable concern. Attempts have previously been made to utilise CID mass spectrometry to investigate protein structures by quantifying deuterium uptake by individual amino acids. However, deuterium scattering has led to a number of questions regarding the validity of the data generated this way as the detected deuterium may have scattered to alternative positions. See, for example, Reed et al. J. Am. Soc. Mass Spec. 12, 1163-1168 (2001).

The impact of deuterium scattering on the use of deuterated internal standards has been studied, showing differences in the amount of scattering observed between deuterated compounds and also between different transitions for the same compound. However, the general conclusion was that deuterated compounds are suitable to use as internal standards despite scattering and that the effects of scattering could be mitigated by selecting appropriate instrument conditions and mass transitions to minimize scattering. See, for example, Cooper et al. Deuterium Scrambling in Clinically Significant Hormones from Multiple Reaction Monitoring (MRM) Experiments at High and Low Concentrations in Solution (2011) and Cooper et al. Evaluation of LCMSMS Deuterium Scrambling in Clinically Significant Small Molecules (2012).

EXAMPLE 1

Identification and Selection of Deuterated Analogs

Based upon available data, and without wishing to be bound by any particular theory, it is believed that deuterium scattering is not generally a random process. One factor potentially affecting scattering is the proximity of the deuterium to polar groups, such as oxygen or nitrogen atoms. Illustrative patterns can be observed from the data comparing scattering for cortisol, d2-cortisol, and d4-cortisol (Table 1 and Formula 1).

TABLE 1

Comparison of deuterium scattering observed for cortisol, d2-cortisol, and d4-cortisol.

| Analyte | Transition | % $D_{n-1}:D_n$ | % $D_{n-2}:D_n$ |
|---|---|---|---|
| Cortisol | 363.25 > 121.0 | 0 | 0 |
| | 363.25 > 309.1 | 0.4 | 0.1 |
| | 363.25 > 327.1 | 0.5 | 0 |
| | 363.25 > 345.1 | 0.5 | 0 |
| d2-Cortisol | 365.25 > 123.0 | 48.3 | 0 |
| | 365.25 > 311.1 | 8.4 | 0.7 |
| | 365.25 > 329.1 | 6.6 | 0 |
| | 365.25 > 347.1 | 7.5 | 0 |
| d4-Cortisol | 367.25 > 121.0 | 0.4 | 0 |
| | 367.25 > 313.1 | 32.1 | 10 |
| | 367.25 > 331.1 | 18.7 | 0 |
| | 367.25 > 349.1 | 6.4 | 0 |

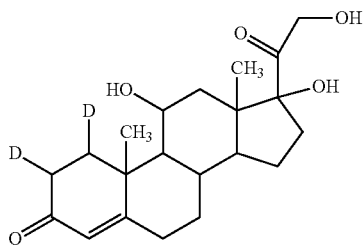

Formula 1

-continued

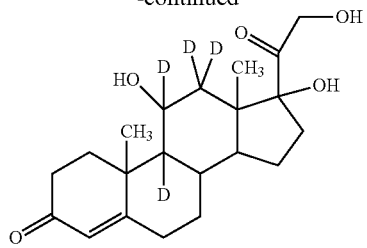

Formula 1. Deuterated (d2- and d4-) Cortisol Structures Used to Generate the Data Shown in Table 1.

All of the listed cortisol transitions, except for 121, are losses of about 18 and are therefore likely to indicate water loss.

For d2-cortisol, the observed water loss scattering is predominantly for that of a single deuterium. This makes sense in context of the d2-cortisol structure, where the deuterium on carbon two is adjacent to the oxygen atom on carbon three (e.g., more likely to scatter), while the deuterium on carbon one is separated from the remaining oxygen atoms attached to carbons 11, 17, 20, and 22 (e.g., less likely to scatter).

For d4-cortisol, all four deuterium atoms are located relatively close to oxygen atoms, which can explain the higher level of scattering observed for the water losses. Also, the amount of scattering observed increases for each additional water loss, suggesting that the prevalence of scattering can increase each time a group fragments from the parent structure. There is also a greater amount of scattering observed for the loss of two deuterium atoms, which would again seem likely due to proximity of the deuterium to the oxygen atoms.

The 121 fragment is a more difficult structure to predict. It retains both the deuterium atoms on the d2-cortisol but loses all the deuterium present on the d4-cortisol, so likely involves rearrangement of carbon ring A. Interestingly there is nearly 50% scattering of deuterium for this fragment for d2-cortisol, which could be due to the presence of the deuterium adjacent to the oxygen atom on carbon three. However, for the d4-cortisol there is minimal deuterium scattering for the equivalent transition.

Based on the foregoing, d4-cortisol is expected to be a better cortisol analog (e.g., internal standard) than d2-cortisol for methods in accordance with the present invention. An example analysis demonstrating the utility of d4-cortisol is discussed in Example 2 below. Additional example inquiries that can be used as a basis for the selection of deuterated analogs according to the invention are discussed in the context for progesterone and testosterone below.

It has been observed that d9-progesterone (Formula 2) exhibits considerable deuterium scattering for the transitions 324.25>306.1 (e.g., single deuterium loss 16.1%, double deuterium loss 0.9%) and 324.25>288.1 (e.g., single deuterium loss 40.4%, double deuterium loss 12.4%). Again, these transitions likely correspond to water loss. d9-progesterone also includes deuterium atoms located in close proximity to both oxygen atoms, which can explain the relatively high incidence of the double deuterium loss for the 324.25>288.1 transition. Based upon the deuterium scattering signature, d9-progesterone is expected to be a suitable analog (e.g., internal standard) for methods in accordance with the present invention. Further experiments, for example the study of further deuterated analogs and/or the relationship between the analog signal and the sample matrix, can be carried out to further refine hypothesized analogs.

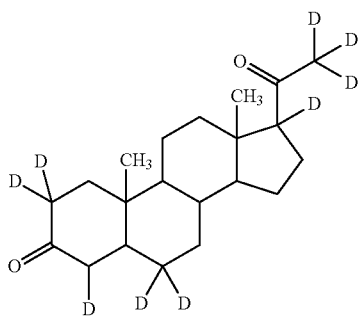

Formula 2. Structure of the Deuterated d9-Progesterone Discussed Above.

It has been observed that d3-testosterone (Formula 3) exhibits >30% scattering for a single deuterium loss using the minor 292>256 transition, which corresponds to a double water loss. However, no scattering was observed for the more commonly used testosterone transitions of 292>97 and 292>109. These two fragments have previously been identified as being made up from carbon rings A and B (see, e.g., Williams et al. J. Mass Spectrom. 34, 206-216 (1999)), which are at the opposite end of the molecule to the three deuterium atoms.

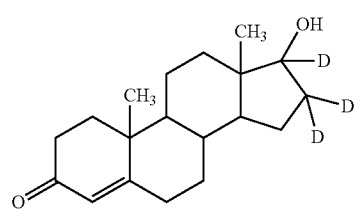

Formula 3. Structure of the Deuterated d3-Testosterone Discussed Above.

In addition to the presence of polar groups proximate to the deuterium, there are a number of other factors that can play a role in deuterium scattering. For example, the charge on a protein can affect the level of scattering observed. If charge affects deuterium scattering, then the position at which the molecule ionizes during mass spectrometry can also impact deuterium scattering. In addition, many compounds undergo complex structural rearrangements during fragmentation—such molecular disruption could also lead to the scattering of deuterium atoms.

Because factors affecting the incidence of deuterium scattering can be hypothesized and/or predicted (to at least some degree of accuracy), it is possible to design analogs of analytes (e.g., internal standards) with deuterium atoms at specific points in the molecule. For example this could be done to minimize the incidence of scattering to improve sensitivity for a deuterated compound. Alternatively, a compound could be deuterated in positions to promote scattering in order to obtain mass transitions novel to deuterated compounds. Once designed, deuterated analogs can be obtained and tested for their compatibility with the analytical methods of the invention.

EXAMPLE 2

Use of Deuterium Scattering in the Analysis of Urinary Free Cortisol by LC/MS/MS Measurement of 24-hour urinary free cortisol (UFC) by liquid chromatography tandem mass spectrometry (LC/MS/MS) is routinely conducted as part of the investigation of suspected hypercortolism associated with Cushing's syndrome. However, urine is a complex matrix containing a number of interferences that behave similarly to the d4-cortisol internal standard in LC/MS/MS. In order to generate accurate data for UFC, it is essential to isolate these interferences from the analyte. Example 2 illustrates how the invention can be used to avoid interferences for a d4-cortisol internal standard by using deuterium scattering to obtain a novel mass transition.

D4-cortisol contains three hydroxyl groups and can undergo triple water loss during MS analysis. Although d4-cortisol should undergo this triple water loss without losing any of its four deuterium atoms, collision induced dissociation during tandem mass spectrometry can lead to scattering of hydrogen atoms. If a deuterium atom is scattered onto a hydroxyl group during CID, it can then be lost from the molecule in the triple water loss. Such scattering and fragmentation creates a unique mass transition, which is highly specific to deuterated cortisol, and which can be used to minimize interferences.

Methods

Preparation of Calibrators:

Calibrators were prepared by spiking cortisol into 1.0 mL aliquots of synthetic urine over the concentration range 0.49-500 ng/mL. The final concentration of the calibrators was 0.49, 1.9, 7.8, 31.3, 125, and 500 ng/mL.

Preparation of QC Samples:

QC samples were prepared by spiking cortisol into 1.0 mL aliquots of urine containing low cortisol concentrations. The final concentration of the QC samples was 0.7, 7.7, and 100.7 ng/mL.

Sample Preparation:

Sample (50 μL) was added to water (150 μL) containing 60 ng/mL d4-cortisol. Samples were then vortex mixed at 1000 rpm for five minutes. Samples were analyzed using automated online solid phase extraction High Pressure Liquid Chromatography-Tandem Mass Spectrometry.

High Pressure Liquid Chromatography-Tandem Mass Spectrometry (HPLC/MS/MS):

Automated online extraction was carried out with a Waters® ACQUITY UPLC® coupled to a Waters MassTrak Online SPE Analyzer using Waters XBridge™ C18 online SPE cartridges washed with water, methanol and 40% aqueous methanol (all commercially available from Waters Technologies Corporation, Milford, Mass., USA). Analytes were eluted onto a 2.1×30 mm Waters HSS SB column using a water/methanol/ammonium acetate gradient and analyzed using a Waters ACQUITY® TQD mass spectrometer. The run time was 5 minutes, with an injection-to-injection time of approximately 5.5 minutes. The chromatography gradient is shown in Table 2, where mobile phase A was 2 mM ammonium acetate and 0.1% formic acid in water and mobile phase B was 2 mM ammonium acetate and 0.1% formic acid in methanol.

TABLE 2

Gradient profile for the analysis of urinary free cortisol.

| Time (min) | Flow Rate (mL/min) | % A | % B | Curve |
|---|---|---|---|---|
| 0 | 0.6 | 63 | 37 | — |
| 4.0 | 0.6 | 55 | 45 | 6 |
| 4.01 | 0.6 | 2 | 98 | 6 |
| 4.5 | 0.6 | 63 | 37 | 11 |

The eluent from the column (in this example, a Waters® ACQUITY UPLC® column) was directed into the electrospray ionization source of a Waters TQD tandem quadrupole mass spectrometer operated in multiple reaction monitoring (MRM) mode. Two MRM transitions were monitored (cortisol and d4-cortisol; see Table 3) using a dwell time of 150 ms.

TABLE 3

MS/MS characteristics of cortisol and d4-cortisol.

| Analyte | MRM Transition | Cone Voltage (V) | Collision Energy (eV) |
|---|---|---|---|
| Cortisol | 363.1 > 121.0 | 30 | 25 |
| d4-cortisol | 367.1 > 312.0 | 30 | 10 |

TargetLynx software was used to perform peak area integration, calculate response (analyte peak area/internal standard peak area ratio), generate a calibration line and calculate the analyte concentration in each sample.

Results and Discussion

Figure 2:
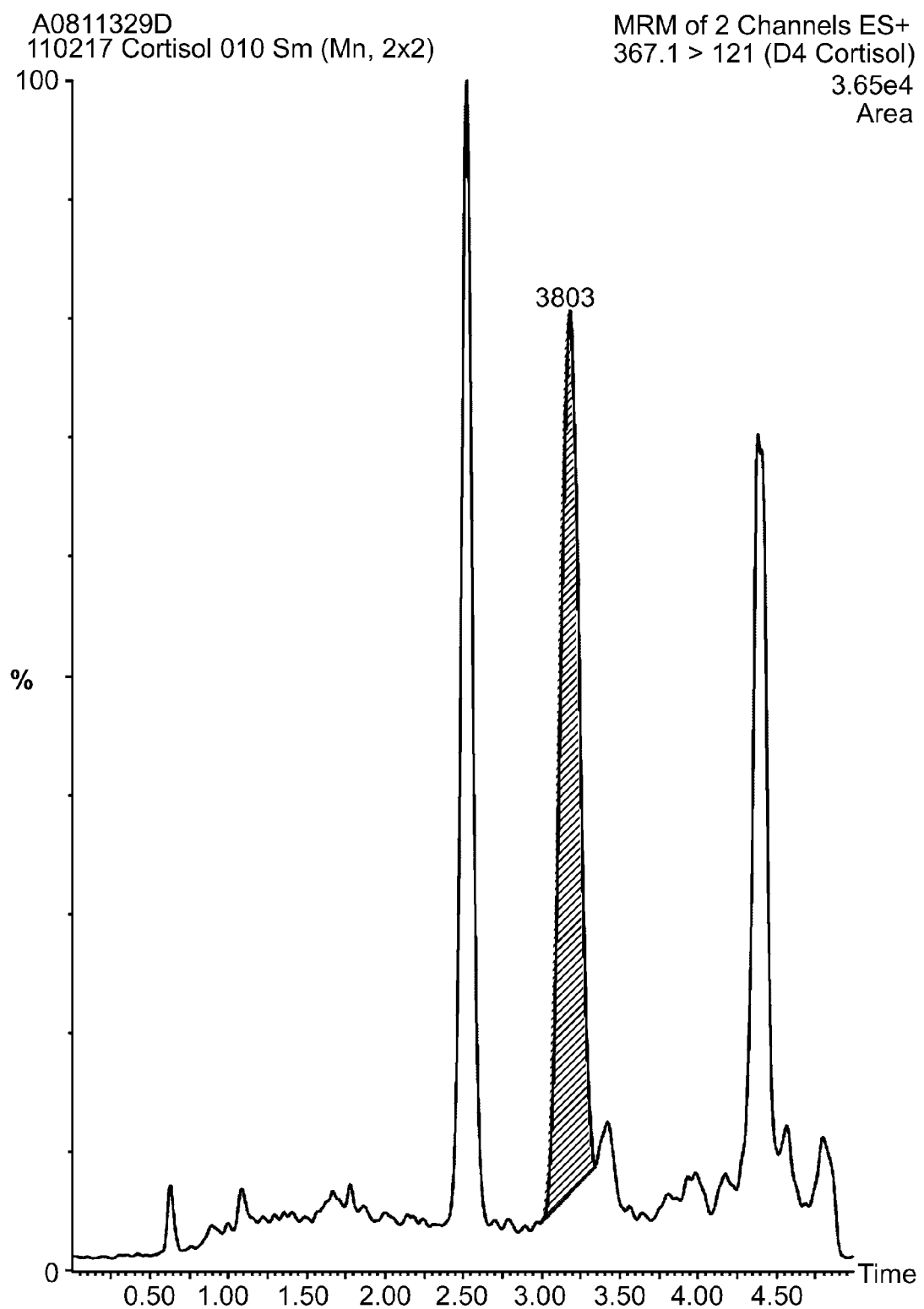
FIG. 2 shows a chromatogram of a urine sample analyzed using the mass transition m/z 367.1>121.1.

FIG. 2 shows a chromatogram of a urine sample analyzed using the mass transition m/z 367.1>121.1. The peak at 3.13 minutes is an interfering peak that masks d4-cortisol, which itself elutes at 3.04 minutes.

Figure 3:
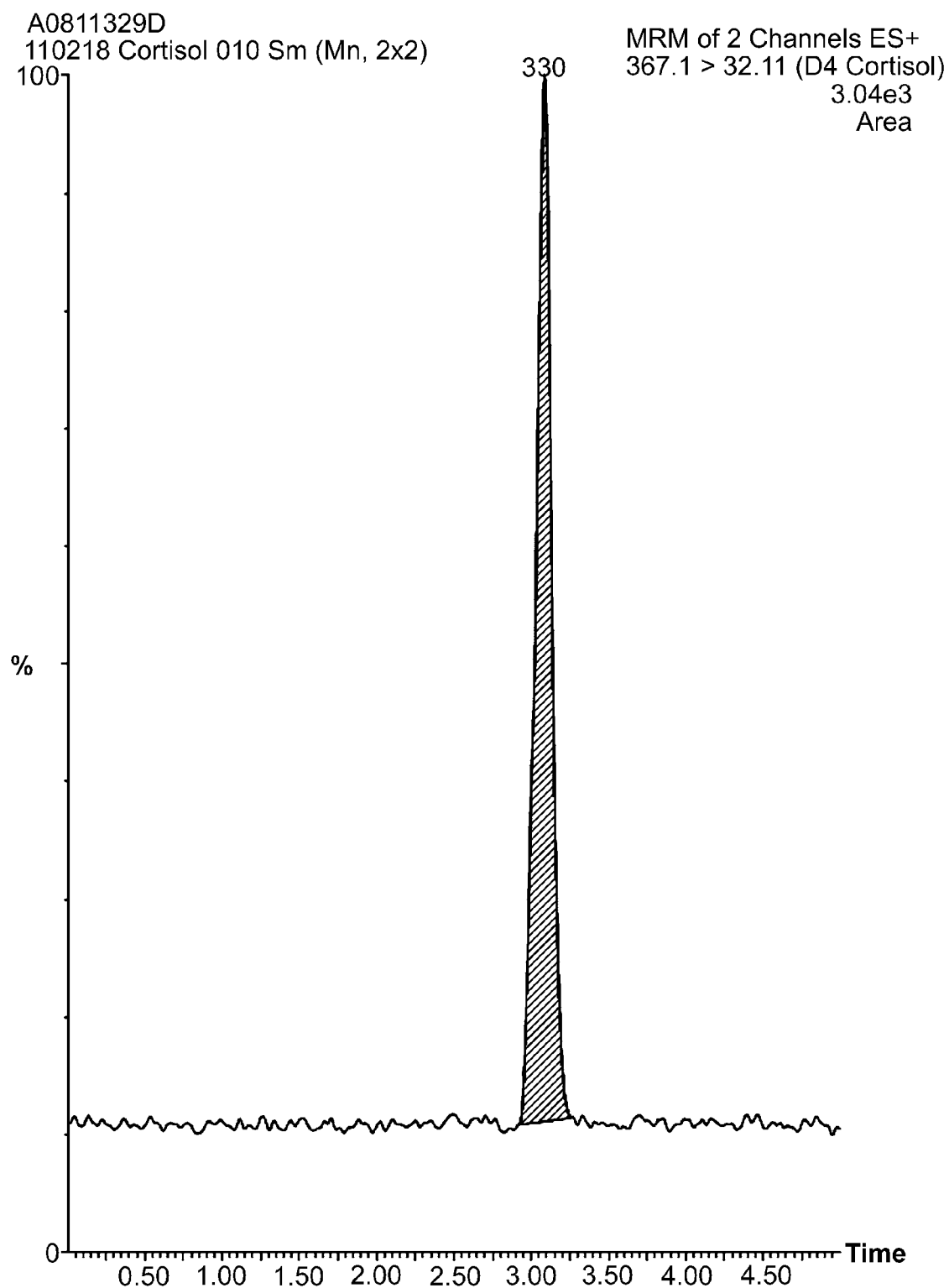
FIG. 3 shows a chromatogram of the same urine sample as used in connection with FIG. 2, but analyzed using the mass transition m/z 367.1>312.1.

FIG. 3 shows a chromatogram of the same urine sample as used in connection with FIG. 2, but analyzed using the mass transition m/z 367.1>312.1, which corresponds to a triple water loss plus one deuterium atom. This transition is highly specific to deuterated cortisol and is free from the interfering peak from the urine.

Figure 4:
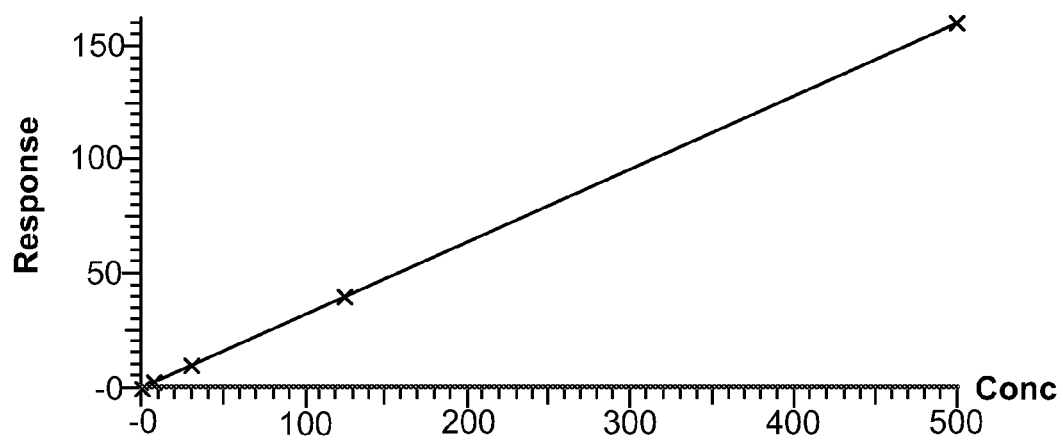
FIG. 4 shows the linearity of an example assay from 0.5 ng/mL to 500 ng/mL.

FIG. 4 shows that the assay was linear at least from 0.5 ng/mL to 500 ng/mL, with a coefficient of determination >0.998 (n=5). The x axis of the graph is in units of ng/mL, and the y axis gives relative response. Table 4 and Table 5 show that the intra-day precision for low, mid and high QCs (0.6, 10 and 100 ng/mL) were all <10% CV (n=5. Coefficient of variation (CV) is a normalized measure of dispersion of a probable distribution, i.e., the ratio of the SD to the mean).

In conclusion, using a deuterium scattered internal standard transition (e.g., as shown in FIG. 3) gave reproducible results that addresses the matrix effects and/or isobaric interferences arising from the analysis of UFC using a d4-cortisol internal standard. The methods of the invention are equally applicable to the analysis of other target analytes in complex matrices by using deuterated analyte analogs that undergo deuterium scattering during MS analysis to overcome interferences that might otherwise interfere with the internal standard signal.

TABLE 4

Intra-day precision for low, mid, and high QCs (0.6, 10 and 100 ng/mL).

| | Day 1 | Day 2 | Day 3 | Day 4 | Day 5 |
|---|---|---|---|---|---|
| | Average Response | | | | |
| Low | 0.17 | 0.15 | 0.15 | 0.17 | 0.15 |
| Mid | 2.59 | 2.39 | 2.38 | 2.57 | 2.34 |
| High | 34.45 | 31.74 | 31.46 | 33.24 | 32.19 |
| | Standard Deviation | | | | |
| Low | 0.01 | 0.01 | 0.01 | 0.01 | 0.01 |
| Mid | 0.05 | 0.04 | 0.11 | 0.09 | 0.09 |
| High | 0.30 | 0.73 | 0.59 | 0.77 | 0.77 |
| | % CV | | | | |
| Low | 6.15 | 5.88 | 3.41 | 5.72 | 7.16 |
| Mid | 1.95 | 1.51 | 4.74 | 3.35 | 3.66 |
| High | 0.87 | 2.30 | 1.88 | 2.33 | 2.39 |

TABLE 5

Averaged precision for low, mid, and high QCs (0.6, 10 and 100 ng/mL).

| | Average Response | Standard Deviation | % CV |
|---|---|---|---|
| Low | 0.16 | 0.01 | 7.91 |
| Mid | 2.45 | 0.13 | 5.26 |
| High | 32.62 | 1.27 | 3.90 |

Recitation of ranges of values herein is merely intended to serve as a shorthand method of referring individually to each separate value falling within the range. Unless otherwise indicated, each individual value is incorporated into the specification as if it were individually recited. Each of the documents cited herein (including all patents, patent applications, scientific publications, manufacturer's specifications, and instructions), are hereby incorporated by reference in their entirety.

The specification should be understood as disclosing and encompassing all possible permutations and combinations of the described aspects, embodiments, and examples unless the context indicates otherwise. One of ordinary skill in the art will appreciate that the invention can be practiced by other than the summarized and described aspect, embodiments, and examples, which are presented for purposes of illustration, and that the invention is limited only by the following claims.

The invention claimed is:

1. A method for determining an amount of an analyte in a sample by mass spectrometry, the method comprising:
    ionizing an analyte from the sample and a deuterated analog of the analyte to produce an analyte ion and a deuterated analog ion, wherein the deuterated analog undergoes fragmentation and deuterium scattering during mass spectrometry;
    selecting a mass transition resulting from fragmentation and deuterium scattering of the deuterated analog;
    measuring an analyte ion signal and a deuterated analog ion signal by mass spectrometry, wherein the deuterated analog ion signal is measured using said mass transition resulting from fragmentation and deuterium scattering; and
    determining an amount of analyte in the sample using the analyte ion signal and the deuterated analog ion signal.

2. The method of claim 1, wherein the mass spectrometry comprises collision induced dissociation (CID) mass spectrometry.

3. The method of claim 1, wherein the deuterated analog ion comprises a fragment ion.

4. The method of claim 3, wherein the fragmentation and deuterium scattering result in the rearrangement of at least one deuterium atom from the fragment ion to a water molecule.

5. The method of claim 3, wherein the fragmentation and deuterium scattering result in the rearrangement of at least one deuterium atom from the fragment ion to a second fragment ion.

6. The method of claim 3, wherein the fragmentation and deuterium scattering result in the rearrangement of at least one deuterium atom from a second fragment ion to the fragment ion.

7. The method of claim 1, wherein the deuterated analog further comprises a non-hydrogen stable isotope label.

8. A method for determining an amount of cortisol in a sample by mass spectrometry, the method comprising:
    ionizing cortisol from the sample and a deuterated cortisol analog to produce a cortisol ion and a deuterated cortisol analog ion, wherein the deuterated cortisol analog undergoes fragmentation and deuterium scattering during mass spectrometry;
    selecting a mass transition resulting from fragmentation and deuterium scattering of the deuterated cortisol analog;
    measuring a cortisol ion signal and a deuterated cortisol analog ion signal by mass spectrometry, wherein the deuterated cortisol analog ion signal is measured using said mass transition resulting from fragmentation and deuterium scattering; and
    determining an amount of cortisol in the sample using the cortisol ion signal and the deuterated cortisol ion signal.

9. The method of claim 8, wherein the deuterated cortisol analog comprises d4-cortisol.

10. The method of claim 9, wherein the mass transition comprises an m/z of about 367>312.

11. The method of claim 8, wherein the deuterated cortisol analog comprises d2-cortisol.

12. The method of claim 11, wherein the mass transition comprises an m/z of about 365>312.

13. A kit for determining an amount of an analyte in a sample by mass spectrometry, the kit comprising:
    a deuterated analog of the analyte, the deuterated analog selected to undergo fragmentation and deuterium scattering during mass spectrometry and exhibit a mass transition resulting from fragmentation and deuterium scattering; and
    instructions for (i) ionizing an analyte from the sample and a deuterated analog of the analyte to produce a analyte ion and a deuterated analog ion, (ii) selecting a mass transition resulting from fragmentation and deuterium scattering of the deuterated analog, (iii) measuring an analyte ion signal and a deuterated analog ion signal by mass spectrometry, wherein the deuterated analog ion signal is measured using said mass transition resulting from fragmentation and deuterium scattering, and (iv) determining an amount of analyte in the sample using the analyte ion signal and the deuterated analog ion signal.

14. The kit of claim 13, wherein the mass spectrometry comprises collision induced dissociation (CID) mass spectrometry.

15. The kit of claim 13, wherein the deuterated analog ion comprises a fragment ion.

16. The kit of claim 13, wherein the fragmentation and deuterium scattering result in the rearrangement of at least one deuterium atom from the fragment ion to a water molecule.

17. The kit of claim 13, wherein the fragmentation and deuterium scattering result in the rearrangement of at least one deuterium atom from the fragment ion to a second fragment ion.

18. The kit of claim 13, wherein the fragmentation and deuterium scattering result in the rearrangement of at least one deuterium atom from a second fragment ion to the fragment ion.

19. The kit of claim 13, wherein the deuterated analog further comprises a non-hydrogen stable isotope label.

20. The kit of claim 13, wherein the deuterated analog comprises a d4-cortisol and the mass transition comprises an m/z of about 367>312.

21. The kit of claim 13, wherein the deuterated analog comprises a d2-cortisol and the mass transition comprises an m/z of about 365>312.

* * * * *